United States Patent [19]

Mougin et al.

[11] Patent Number: 5,643,581
[45] Date of Patent: Jul. 1, 1997

[54] COSMETIC COMPOSITIONS AND THEIR USES

[75] Inventors: Nathalie Mougin, Paris; Jean Mondet, Drancy, both of France

[73] Assignee: L'Oreal, Paris, France

[21] Appl. No.: 280,875

[22] Filed: Jul. 27, 1994

[30] Foreign Application Priority Data

Jul. 28, 1993 [FR] France .................. 93 09286

[51] Int. Cl.$^6$ .................. A61K 7/06; A61K 7/04
[52] U.S. Cl. .................. 424/401; 424/47; 424/59; 424/61; 424/70.1; 424/70.7
[58] Field of Search .................. 424/47, 401, 59, 424/61, 70.7, 70.1

[56] References Cited

U.S. PATENT DOCUMENTS 4,962,178  10/1990  Harisiades .................. 528/83

FOREIGN PATENT DOCUMENTS

WO91/17215  11/1991  France .

OTHER PUBLICATIONS

Kossmehl et al., "Hydrophilic Silicone Rubber Materials Containing Dimethylsiloxane And Urethane Moieties In The Main Chain," Jun. 1986, Makromol. Chem. vol. 187, pp. 1371–1380.

Otsuki et al., "Synthesis And Properties Of New Poly(dimethylsiloxane)–Urea–Polyamide Multiblock Copolymers By Diisocyanate Method," Polymer Journal, vol. 24, No. 4, Apr. 15, 1992, pp. 347–355.

Primary Examiner—Jyothsan Venkat
Attorney, Agent, or Firm—Finnegan, Henderson, Farabow, Garrett & Dunner, L.L.P.

[57] ABSTRACT

New cosmetic compositions characterized in that they comprise, in a cosmetically acceptable carrier, at least one pseudolatex based on a multiblock polycondensate which contains a polysiloxane block and a polyurethane and/or polyurea block, wherein the polyurethane and/or polyurea block further comprises anionic or cationic groups. These compositions can be employed especially in the cosmetic field of hair care, of make-up or of skin care.

44 Claims, No Drawings

5,643,581

COSMETIC COMPOSITIONS AND THEIR USES

The present invention relates to new cosmetic compositions and to some of their particular applications. More precisely, it relates to new cosmetic compositions with film-forming properties, containing particular pseudolatices, and to their uses, especially in the field of cosmetic (i.e., topical) treatments of the skin, of hair, of nails and of other keratinous substances.

It is commonplace to use in cosmetic formulations, in particular in hair-care products (shampoos, after-shampoos, hair-styling or treating lotions or gels, hair-forming, sculpting or setting lacquers or lotions, and the like) or in make-up products (such as, for example, nail varnishes, mascaras, eyeliners and others), in a proportion which can vary depending on the nature and the purpose of the formulation, at least one film-forming substance which makes it possible, or is aimed at, imparting certain improved characteristics to the substrate on to which it is applied (that is to say, in this case, one of the parts of the body's surface, such as hair, eyelashes, body hair, skin, nails, etc.). Thus, for example, in the particular case of the treatment of a head of hair, what is looked for above all using this technique is more firmness and more softness in the case of hair, whereas in the more particular case of the nails, the objective is chiefly to obtain a shiny and hard protective film adhering perfectly to the latter.

In recent years a very particular interest has been displayed in the production of film-forming cosmetic compositions of aqueous type, this being with the aim of replacing, especially for safety and environmental reasons, the usual film-forming substances present in organic substrates (in particular alcohols).

It is thus now known to employ, in some cosmetic compositions, latices (that is to say aqueous colloidal dispersions of polymer particles) containing polyurethanes or acrylic polymers as film-forming resins. For example, Patent Application EP-A-418,469 has described nail varnish compositions containing aqueous dispersions of aliphatic polyurethanes and Patent Application EP-A-391,322 has described nail varnishes containing an aqueous dispersion of a polyurethane and/or of a polyurethane copolymer.

To be satisfactory in cosmetic applications, a film-forming resin must exhibit certain constraining characteristics or properties, among which there may be mentioned more particularly, no limitation being implied thereby, first of all a very good affinity/compatibility/harmlessness towards the various keratinous matters (skin, hair and others), next, good film-forming properties in relation to the latter (quality and uniformity of the deposited film) and, finally, good durability properties (adhesiveness, toughness), that is to say that it must be difficult to remove from its substrate merely by washing with water or, for example, with the aid of detergents (shampoos). In the case of nail varnishes the film must furthermore have a good resistance to mechanical abrasion. In general it will be noted that it is often difficult, in practice, to find a film-forming substance which is capable of being actually suitable to a number, or to all, of the various applications that can be cosmetically envisaged for the latter (problem of the acceptable compromise). In some respects the film-forming substances known hitherto, and in particular those mentioned above, are not suitable for obtaining compositions exhibiting good cosmetic properties, especially because of a marked lack of durability, in particular of resistance to water.

Another problem lies in the fact that the films thus obtained have an insufficient sheen, particularly in the context of applications of the hair care or mascara type. This sheen is furthermore only poorly durable, that is to say that it disappears quickly under the effect of external agents (high sensitivity to water in particular). On the other hand, sheen and the durability of this sheen, are nowadays a property which is particularly sought-after in the cosmetics field.

It can be seen, therefore, that a considerable need exists at present in the state of the art for the ability to have available film-forming compositions which combine, and which do so over a varied range of possible applications (hair, eyelashes, skin, nails, etc.), all the advantages which are generally sought-after or desirable in cosmetics, namely especially harmlessness towards keratinous matter, ease of application and of use, production of fine and uniform protective deposits, durability of the adhesive properties, contribution and durability of the sheen properties, contribution of softness and of lubrication, of rigidity and of resistance to abrasion. The present invention is aimed precisely at satisfying such a need.

Thus, as a result of extensive research into this question, the inventors have found, unexpectedly and surprisingly, that it is possible to obtain film-forming cosmetic compositions which are suited for many applications and which exhibit excellent properties, in particular such as those listed above, by employing certain pseudolatices. This discovery forms the basis of the present invention.

In accordance with the present invention, new cosmetic compositions are therefore now proposed, which are characterized in that they comprise, in a cosmetically acceptable carrier, at least one pseudolatex based on a multiblock polycondensate which comprises, as a first component, a polysiloxane block and, as a second component, a polyurethane and/or polyurea block, said second component further comprising anionic or cationic groups. The choice of an appropriate cosmetically acceptable carrier depends on the purpose of the cosmetic composition, whether it be a nail varnish, mascara, hair care composition, etc. One skilled in the art can routinely choose an acceptable carrier for a specific cosmetic purpose.

According to the invention, and conforming to what is generally accepted, the expression "pseudolatex" is intended to denote a stable aqueous suspension containing fine, generally spherical, particles of the polysiloxane/polyurethane polycondensate as defined above, these particles having been obtained by dispersing, in an appropriate aqueous phase, the said polycondensate in the already synthesized state. The expression "pseudolatex" must not therefore be confused with the expression "latex" or "synthetic latex" which is undoubtedly also an aqueous suspension consisting of particles of a polymer or of a polycondensate, but in which the said particles have been conventionally obtained directly by emulsion polymerization (or polycondensation) of one or more monomers in an appropriate aqueous phase. In particular, the synthesis of a "latex" necessarily requires the use of surface-active agents, which are then still present in the final suspension. In contrast, bearing in mind the ionic nature of the polycondensates used within the scope of the invention, such a use can be dispensed with. This important point will be touched upon again in detail in what follows.

For a good understanding of the description which is to follow, and in particular of the definition of the formulae which are given, an explanation will be given to begin with, though only to outline its main directions, of the general process of synthesis of the pseudolatices employed within the scope of the present invention. The details of the process will be given later. Similarly, the meanings and values of certain radicals (R, B, etc.), and other parameters, will be detailed later and will therefore appear in the introductory part given now only purely by way of symbols and for convenience.

As indicated above, this synthesis therefore first of all involves the preliminary preparation of the polycondensate intended to be made into a suspension. This polycondensate is preferably prepared by a two-stage process. The first stage consists of a conventional polycondensation reaction between (i) a polysiloxane (or silicone) polymer containing a hydroxyl functional group or an amine functional group at the ends of its chain (i.e., an $\alpha,\omega$-dihydroxypolysiloxane or an $\alpha,\omega$-diaminopolysiloxane or an $\alpha,\omega$-aminohydroxy- or hydroxy-aminopolysiloxane) and (ii) a diisocyanate (present in stoichiometric quantity or in stoichiometric excess, that is to say with more than 2 moles per mole of silicone), whereby a new silicone is obtained, this time containing an isocyanate functional group at each of its chain ends; then, in a second stage, the chains of the polycondensate obtained above are coupled by means of a coupling agent (in variable quantity chosen as a function of the desired final chain length) which is chosen from diols and/or diamines and/or alcoholamines, so as to obtain ultimately a new polycondensate with a longer chain.

The reactions used in the first stage thus produce a polysiloxane which, in addition to the above-mentioned isocyanate functional groups, has urethane and/or urea units at its chain ends, this being according to the conventional mechanisms of a condensation reaction performed between (i) an isocyanate functional group, as carried by the starting diisocyanate, and (ii) an alcohol functional group (in this case creation of a urethane unit) or an amine functional group (in this case formation of a urea functional group), such as are carried by the starting polysiloxane, namely:

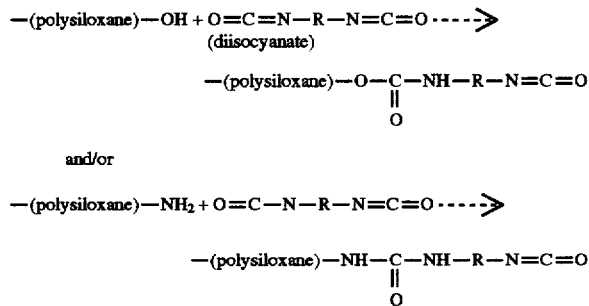

The polycondensates obtained at the outcome of this first stage can therefore in fact be defined by the following general formula (1):

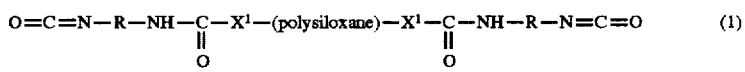

wherein $X^1$, each of which can be identical or different, can therefore denote —O— or —NH—.

In the second stage the alcohol and/or amine functional groups of the coupling agent (which coupling agent can be conveniently symbolized here by OH—B—OH or NH$_2$—B—NH$_2$ or else NH$_2$—B—OH) then react, doing so according to the same mechanisms as those described for the first stage, either with the isocyanate functional groups carried at the end of a chain by the polysiloxane polycondensate of formula (1) above, or with isocyanate functional groups carried by free diisocyanate, when the latter has been introduced in stoichiometric excess during the first stage, thus giving rise in the (longer) chain of the new polycondensate obtained to a succession of urethane and/or urea units, that is to say to blocks of polyurethane and/or polyurea type which can be symbolized by the formula (2):

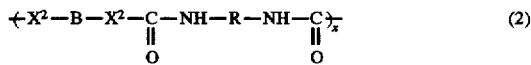

in which $X^2$ denotes —O— or —NH— and x is a value corresponding substantially to the number of moles of coupling agent introduced into the reaction.

As indicated above, a polycondensate is thus finally obtained which consists of the repetition of polysiloxane blocks (corresponding simply to the initial polysiloxane in the form shown in formula (1)) and of polyurethane and/or polyurea blocks (formula (2)).

According to an highly preferred aspect of the invention the coupling agents (that is to say, in fact, the radical B) carry chemically anionizable or cationizable groups, that is to say groups which, respectively, give anionic groups when subjected to the action of a base (this is the case, for example, with carboxylic groups) and give cationic groups when subjected to the action of an acid (for example in the case of a tertiary amine). The neutralization of the anionizable (or cationizable) groups by the base (or by the acid) can then be, at will, either partial or complete, depending on the quantity of neutralizing agents introduced.

The ionizable (and after neutralization ionized) nature of the polycondensate thus makes it possible to dispense with the use of surface-active ingredients during the preparation of the corresponding pseudolatices (autodispersibility). These pseudolatices are obtained by conventional and known methods for the preparation of pseudolatices, except, however, for certain highly preferred features which will be mentioned in more detail in what follows. In particular, it can be emphasized again that the pseudolatices in accordance with the invention exhibit a more or less marked ionic nature.

However, other characteristics, aspects and advantages of the invention will now appear more clearly on reading the detailed and complete description which is to follow, as well as various concrete examples intended to illustrate it, but without any limitation being implied thereby.

As indicated above, the chain of the ionic polycondensate forming part of the composition of the pseudolatices employed within the scope of the present invention consists of the repetition (or alternation) of blocks of polysiloxane type and of blocks of polyurethane type and/or polyurea type, the said polyurethane and/or polyurea blocks containing ionic groups of anionic or cationic type.

The repetition of the above blocks may be of random type, but is preferably of uniformly alternating type. Furthermore, the number ratio of the blocks of polyurethane and/or polyurea type to the blocks of polysiloxane type is generally from 1:1 to 10:1, preferably from 1:1 to 3:1.

The molecular weights of the polysiloxane-polyurethane/polyurea polycondensates may vary within wide limits, such as from 2000 to 500,000, but more preferably from 3000 to 250,000.

The polysiloxane block preferably corresponds to the following general formula (I):

$$\text{---}[\text{---}X^1\text{---}P\text{---}X^1\text{---}]\text{---}\underset{\underset{O}{\|}}{C}\text{---}NH\text{---}R\text{---}NH\text{---}\underset{\underset{O}{\|}}{C}\text{---} \quad (I)$$

in which:

P is a polysiloxane block, $X^1$, each of which can be identical or different, denotes —O— or —NH—, and R (which is none other than the unit of the diisocyanate as referred to above) is a divalent radical chosen from alkylene radicals of aromatic, aliphatic or cycloaliphatic type.

The polysiloxane block P preferably corresponds to the following general formula (I'):

$$-Y\!-\!\!\left[\begin{array}{c}R^1\\|\\Si\!-\!O\\|\\R^1\end{array}\right]_{\!z}\!\!\begin{array}{c}R^1\\|\\Si\!-\!Y-\\|\\R^1\end{array} \quad (I')$$

in which the radicals $R^1$, which may be identical or different, are chosen from, on the one hand, substituted and unsubstituted monovalent nonaromatic $C_1$–$C_{20}$ hydrocarbon radicals free from or substantially free from ethylenic unsaturations and, on the other hand, aromatic radicals, Y denotes a divalent hydrocarbon radical and z is an integer such that the mean molecular weight of the polysiloxane block ranges from 300 to 10,000. In other words, either all $R^1$ radicals are independently selected from monovalent nonaromatic $C_1$–$C_{20}$ hydrocarbon radicals free from or substantially free from ethylenic unsaturations or all $R^1$ radicals are independently selected from aromatic radicals.

Y is preferably a divalent radical chosen from alkylene radicals of formula —$(CH_2)_a$—, in which a denotes an integer which may vary from 1 to 10.

By way of radicals $R^1$ which are suitable within the scope of the invention there may be mentioned more particularly alkyl radicals and especially methyl, ethyl, propyl, isopropyl, butyl, pentyl, hexyl, octyl, decyl, dodecyl and octadecyl radicals, cycloalkyl radicals, in particular the cyclohexyl radical, aryl radicals, especially phenyl and naphthyl, arylalkyl radicals, especially benzyl and phenylethyl, and tolyl and xylyl radicals. It will be noted that, according to the invention, the polysiloxane block should be free, or substantially free, of units of the Si—H or Si—$R^1$ type in which $R^1$ would denote a hydrocarbon radical containing ethylenic unsaturations, this being so as to avoid any untimely crosslinking of the polycondensate with itself.

According to a particularly preferred embodiment of the present invention, the polysiloxane block P present in the polycondensate forming the pseudolatex corresponds to the following formula ( I" ):

$$\text{---}[CH_2]_a\text{---}\!\!\begin{array}{c}CH_3\\|\\Si\!-\!O\\|\\CH_3\end{array}\!\!\left]_{\!z}\!\!\begin{array}{c}CH_3\\|\\Si\!-\![CH_2]_a\text{---}\\|\\CH_3\end{array} \quad (I'')$$

in which a and z are values as defined above.

Turning now to deal with the polyurethane and/or polyurea blocks forming part of the constitution of the polycondensates which are employed within the scope of the invention, these preferably correspond to the following general formula (II):

$$\text{---}[\text{---}X^2\text{---}B\text{---}X^2\text{---}\underset{\underset{O}{\|}}{C}\text{---}NH\text{---}R\text{---}NH\text{---}\underset{\underset{O}{\|}}{C}\text{---}]_x\text{---} \quad (II)$$

in which:

$X^2$ each of which can be identical or different denotes —O— or —NH—,

R (which, as before in formula (I), is none other than the unit of the diisocyanate employed for conducting the condensation reaction) is as defined above for the blocks of formula (I), x (which, as indicated above in the description corresponds substantially to the number of moles of coupling agents employed in the process of synthesis of the polycondensate) is an integer which can preferably vary from 1 to 10 and more preferably from 1 to 3, and B (which is none other than the unit introduced by the coupling agent as mentioned above) is a divalent radical carrying a positive or negative ionic charge. A preferred divalent radical carrying a negative ionic charge is a divalent hydrocarbon radical.

By way of radicals B carrying anionic groups (i.e., negative charges) there may be mentioned more particularly those carrying a group containing one or more carboxylic functional groups and/or one or more sulphonic functional groups, said carboxylic and/or sulphonic functional groups being partially or completely neutralized with an inorganic or organic base, as will be explained in more detail in what follows, to provide a negative ionic charge.

Thus, among the divalent radicals B carrying carboxylic or sulphonic functional groups which are particularly suitable within the scope of the present invention there may be mentioned those of formula (III):

$$\text{---}[CH_2]_p\text{---}\underset{\underset{Z}{|}}{\overset{\overset{R^2}{|}}{C}}\text{---}[CH_2]_q\text{---} \quad (III)$$

in which $R^2$ denotes a $C_1$–$C_3$ linear or branched alkyl radical, Z is a carboxylic acid anion (—COO$^-$) or a sulphonic acid anion (—SO$_3^-$) respectively obtained from a carboxylic acid or sulphonic acid functional group or a salt of said acid functional groups (carboxylate and sulphonate functional groups respectively), and p and q, which may be identical or different, are integers ranging from 1 to 5, and those of formula (III'):

$$\text{[benzene ring]}\text{---}Z \quad (III')$$

in which Z has the above meaning.

By way of radicals B carrying cationic groups (i.e., positive charges) there may be mentioned more particularly those carrying groups of tertiary amine type, said tertiary amines being partly or completely either neutralized (presence of —NH$^+$— units) or quaternized, as will be explained in greater detail in what follows.

Thus, among the divalent radicals B carrying cationizable tertiary amine functional groups which are particularly suitable within the scope of the present invention there may be mentioned those of formula:

$$\text{---}[CH_2]_r\text{---}\underset{\underset{R^3}{|}}{N}\text{---}[CH_2]_s\text{---} \quad (IV)$$

in which $R^3$ denotes a $C_1$–$C_4$ linear or branched alkyl radical and r and s are identical or different integers which may vary from 1 to 10.

In neutralized or quaternized form the radicals B above then become:

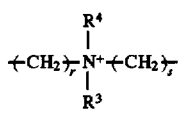 (IV')

in which formula R³ has the above meaning and R⁴ denotes either hydrogen (neutralization) or a $C_1$–$C_{10}$ linear or branched alkyl radical or an aromatic ring (quaternization).

According to the invention the degrees of neutralization of the anionizable or cationizable functional groups may preferably range from 10 to 100%, more preferably from 20 to 100%.

Finally, concerning the radicals R which are more particularly preferred according to the present invention and are included within the scope of the definition of the blocks of formulae (I) and (II) as given above, there may be mentioned those of formulae:

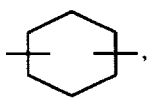,

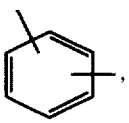,

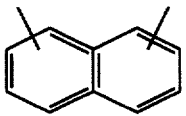

or

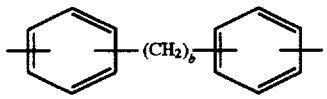

or

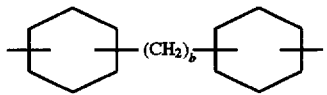

or

in which b is an integer from 0 to 3 and c is an integer from 1 to 20, preferably from 2 to 12.

Among the divalent radicals R which are particularly preferred and included within the scope of the above formulae, there may be mentioned hexamethylene, 4,4'-biphenylenemethane, 2,4- and/or 2,6-tolylene, 1,5-naphthylene, p-phenylene and 4,4-methylenebiscyclohexyl radicals and the divalent radical derived from isophorone.

The process of synthesis of the pseudolatices employed within the scope of the present invention will now be developed in slightly greater detail. In its major outlines this process corresponds to that already indicated at the beginning of the description.

An α,ω-dihydroxy- and/or diamino- and/or aminohydroxy- and/or hydroxyaminopolysiloxane corresponding to the following general formula:

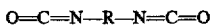

in which P has the meaning given above (polysiloxane block) and $X^3$, each of which can be identical or different, denotes —OH or —NH₂, is reacted, in an organic solvent, with a stoichiometric excess of a diisocyanate of formula:

$$O=C=N-R-N=C=O$$

in which R has the meaning given above, and then the chains of the polycondensate obtained above are coupled with a diol and/or a diamine and/or an alcoholamine corresponding to the formula:

in which B has the meaning given above and $X^4$ denotes —OH or —NH₂, at a temperature of between 40° and 100° C., in the presence of a tin salt as catalyst.

The organic solvent employed in these stages is preferably chosen from acetone, methyl ethyl ketone, tetrahydrofuran and 1,2-dichloroethane, these solvents being inert towards isocyanate groups. The tin salt, for its part, is preferably chosen from tin 2-ethylhexanoate and dibutyltin dilaurate.

Within the scope of the embodiment of the above process the diisocyanates which are particularly preferred are chosen, by themselves or as mixtures, from 4,4'-diphenylmethane diisocyanate and 4,4'-methylenebisdicyclohexyl diisocyanate, and the coupling agents which are particularly preferred are chosen, by themselves or as mixtures, from dimethylolpropionic acid, N-methyldiethanolamine, 1,3-diaminopropane and ethanolamine, it being clearly understood that the possibility of acid coupler/amine coupler mixture is ruled out.

The polysiloxane-polyurethane/polyurea polycondensate thus obtained can next be optionally purified, for example by precipitation into a nonpolar solvent such as cyclohexane.

In accordance with the invention, this polycondensate, optionally purified, is next employed for the preparation of a stable pseudolatex which will consist of solid particles of the polycondensate neutralized with the aid of a suitable neutralizing agent which may be either an inorganic or organic base when the radical B as defined above carries anionizable functional groups such as, for example, carboxylic and/or sulphonic acid functional groups, or an inorganic or organic acid when said radical B carries cationizable functional groups such as, for example, tertiary amine functional groups, or an alkyl halide with a view specifically to perform the quaternization of tertiary amines. According to the invention the degree of neutralization preferably ranges from 10% to 100%, more preferably from 20 to 100%.

A conventional process for the preparation of pseudolatices, consists in dissolving a water-insoluble polymer in an organic solvent which is soluble or partially soluble in water, introducing into the organic solution of polymer which is thus obtained a surfactant, a mixture of surfactants or a protective colloid polymer or else a surfactant(s)/protective colloid polymer mixture, this being with the aim of obtaining good stabilization of the particles, and then dispersing (emulsion) with stirring the dispersion thus obtained in water and next performing the removal of the organic solvent by vacuum evaporation, which produces an aqueous suspension of polymer particles which are coated with surfactant(s) and/or protective colloid polymer. In contrast, the polycondensates containing polysiloxane-polyurethane/polyurea blocks employed within the scope of the invention make it possible to obtain pseudolatices which are particularly stable in the absence of any hydrophilic stabilizer, surfactant or protective colloid, since they contain ionic functional groups partially or completely neutralized, providing the polycondensates with a kind of "autodispersibility" in water.

It is obvious that the nature of the neutralizing agent which it will be appropriate to employ to neutralize the polysiloxane-polyurethane/polyurea polycondensate will be a function of the nature of the ionizable functional groups carried by the latter.

When said polycondensate contains an anionizable functional group such as, for example, a carboxylic or sulphonic acid functional group, the neutralizing agent may be an inorganic base such as sodium hydroxide, potassium hydroxide or aqueous ammonia, or an organic base such as aminoalcohol chosen especially from 2-amino-2-methylpropanol (AMP), triethanolamine, triisopropanolamine (TIPA), monoethanolamine, diethanolamine, tri[(2-hydroxy)-1-propyl]amine, 2-amino-2-methyl-1,3-propanediol (AMPD) and 2-amino-2-hydroxymethyl-1,3-propanediol or else a diamine such as lysine.

When the polycondensate contains a cationizable functional group of the tertiary amine type, the neutralizing agent may be an inorganic acid such as hydrochloric acid or an organic acid such as lactic acid, glycolic acid or mandelic acid. The neutralizing agent may also be a quaternizing agent for the tertiary amine functional group, such as, for example, alkyl halides and in particular methyl iodide or ethyl bromide.

The neutralization may be carried out either in situ in the solution of the polysiloxane- polyurethane/polyurea polycondensate in the organic solvent, by adding the determined quantity of neutralizing agent, or during the preparation of the emulsion, the neutralizing agent being then in the aqueous phase of the emulsion.

The organic solvent employed must be a volatile solvent or a mixture of such solvents which has a boiling point lower than that of water and must furthermore be miscible or partially miscible with water. Such an organic solvent is preferably chosen from acetone, methyl ethyl ketone, tetrahydrofuran, methyl acetate, ethyl acetate, isopropanol and ethanol.

After the polysiloxane-polyurethane/polyurea polycondensate which is completely or partially neutralized in the organic solvent is obtained, the preparation of an emulsion is then undertaken by pouring, with stirring, into the organic solution obtained, an appropriate quantity of water optionally containing an antifoaming agent the purpose of which will be to facilitate the subsequent evaporation of the organic phase.

As indicated above, according to an alternative form of the process, the neutralization of the ionizable functional groups in the polycondensate may be performed during the actual formation of the emulsion by pouring in an aqueous solution containing the required quantity of the neutralizing agent.

During the formation of the emulsion the stirring is preferably carried out with the aid of a shearing disperser of the Moritz or Ultraturax or Raineri type equipped with deflocculating blades.

The emulsion thus obtained is particularly stable without it being necessary to employ a surface-active agent in so far as the ionic groups of the polysiloxane-polyurethane/polyurea polycondensate take up a position at the interface with water and protect the droplets against coalescence by electrostatic repulsion.

After formation of the emulsion at a temperature preferably ranging from the ambient temperature to approximately 70° C., the evaporation of the organic solvent is then undertaken at reduced pressure until it is completely removed, the evaporation being preferably carried out with slight heating.

A pseudolatex is thus finally obtained, that is to say an aqueous dispersion of particles of the film-forming polysiloxane-polyurethane/polyurea polycondensate which can be free from any surfactant or of any other hydrophilic stabilizer, while being very stable.

The mean size of the particles forming the pseudolatex and their polydispersity may be adjusted by varying the respective proportions of the polycondensate, the organic solvent and the water during the preparation of said pseudolatex or by varying the degree of neutralization or the nature of the neutralizing agent.

According to a particular embodiment of the pseudolatices employed within the scope of the present invention the mean size of the particles forming said pseudolatex is from 5 to 400 nanometers, preferably from 10 to 250 nanometers. The size polydispersity of said particles, measured by quasielastic light scattering is, for its part, generally lower than 0.5 and preferably lower than 0.3.

As indicated above, the cosmetic compositions according to the invention, which therefore contain pseudolatices as defined above, in a cosmetically acceptable substrate, can exhibit, for applications as varied as those encountered, for example, in the field of hair care, of make-up, of skin care, or of any other cosmetic field in which the use of a film-forming substance is desirable or sought-after, properties which are quite remarkable, in particular with respect to their film-forming and sheen properties, their ability to retain these properties over time in the face of the action of external agents (durability) and also with respect to their softness, lubrication and abrasion resistance properties.

Among the applications which are preferentially aimed at by the present invention, and the different beneficial effects obtained therein, there may be mentioned more particularly:

the field of hair care products (hair washing, care or beauty), where the compositions according to the invention, in particular in the form of aerosols, of mousse, of shampoos, of after-shampoos, of styling or treating lotions or gels, of shaping or sculpting or setting laquers or lotions, make it possible to give the hair sheen, softness, ease of styling (a phenomenon of "individualization" of the hair at the time when the composition is deposited), better feel and durability (that is to say the durable retention, even under the action of external agents) of these properties;

the field of make-up products, in particular for the making-up of nails and eyelashes, where the compositions according to the invention, for example in the form of nail varnishes, of mascaras or of eyeliners, make it possible to introduce, in the case of make-up for eyelashes, the same advantages as those previously referred to for hair treatment and, in the case of nail varnishes (where the compositions can be employed as film-former alone or as film-forming additive), gloss, better wettability of the nail, durability of the film and of its sheen in washing, better abrasion resistance (contribution of slip by lubrication of the surfaces) and better rigidity;

in the field of skin-care products (creams, milks, lotions, masks, serums, sun products) where the compositions according to the invention make it possible more particularly to contribute sheen, better wettability and resistance to washing with water (sun products).

The proportion of pseudolatex in the cosmetic compositions (apart from nail varnishes) is preferably from 0.5 to 20%, and more preferably from 1 to 15% by weight relative to the total weight of the composition. In the case of nail varnishes this proportion can go up to 30% by weight. In addition, and obviously, the compositions may contain various adjuvants intended to make them acceptable in a particular cosmetic application.

The compositions according to the invention may contain UV-A or UV-B or wide-band sunscreens and may be employed as antisun products.

The compositions according to the invention may furthermore contain conventional cosmetic additives chosen from fatty substances, organic solvents, silicons, thickening agents, softeners, antifoaming agents, hydrating agents, moisturizers, treating agents (antiloss, antidandruff agents, etc), anionic, nonionic or amphoteric polymers or their mixtures, antiperspirants, alkalifying agents, dyes, pigments, perfumes, preserving agents and propellent agents when the compositions are presented in aerosol form.

More precisely, the fatty substances which may be employed are an oil or a wax or their mixtures, fatty acids, fatty alcohols, fatty acid esters such as the triglycerides of $C_6$–$C_{18}$ fatty acids, Vaseline, paraffin wax, lanolin or hydrogenated or acetylated lanolin.

Among the oils there may be mentioned mineral, animal, vegetable oils or synthetic oils and especially vaseline oil, liquid paraffin, castor, jojoba and sesame oils, as well as silicone and isoparaffin oils and gums.

Among the animal, fossil, vegetable, mineral or synthetic waxes there may be mentioned especially beeswax, carob and candelilla wax, ozokerite, microcrystalline waxes and silicone waxes and resins.

Among the thickening agents there may be mentioned:

modified celluloses such as hydroxyethyl cellulose, methyl cellulose, hydroxypropyl cellulose and carboxymethyl cellulose. Among these there may be mentioned especially the gums sold under the name of "Cellosize QP 44001H" by the Amercol company, carob gum, guar gum, quaternized guar gum sold under the name of "Jaguar C-13-S" by the Meyhall company, hydroxypropyl guar gum and xanthan gum, crosslinked polyacrylic acids such as the "Carbopols" from the Goodrich company, glyceryl poly(meth)acrylate polymers sold under the names of "Hispagel" or "Lubragel" by the Hispano Quimica or Guardian companies, polyvinylpyrrolidone, polyvinyl alcohol, crosslinked acrylamide polymers and copolymers such as those sold under the names of "PAS 5161" or "Bozepol C" by the Hoechst company, "Sepigel 305" by the Seppic company, or "Salcare SC95" by the Allied Colloid company, or else the crosslinked methacryloyloxyethyltrimethylammonium chloride homopolymers sold under the name of "Salcare SC95" by the Allied Colloid company.

A number of examples of preparation of polysiloxane-polyurethane polycondensates and of pseudolatices and of cosmetic compositions containing them will now be given by way of illustration of the invention.

The syntheses resulting in the polysiloxane-polyurethane multiblock polycondensates have been carried out starting with prepolymers of the α,ω-hydroxyorganofunctional poly-dimethylsiloxane type (commercial products sold by the Goldschmidt company under the names Tegomer H-Si 2111 and Tegomer H-Si 2311) of structure:

$$HO{\leftarrow}CH_2{\rightarrow}_6{\leftarrow}Si(CH_3)_2-O{\rightarrow}_z Si(CH_3)_2{\leftarrow}CH_2{\rightarrow}_6 OH$$

and additionally having the characteristics which are listed in the table below:

| Trade name | Tegomer H-Si 2111 | Tegomer H-Si 2311 |
|---|---|---|
| Functional groups | Primary hydroxyl groups | |
| Functionality | 2 | 2 |
| Number of z units | approximately 10 | approximately 30 |
| Hydroxyl value (mg KOH/G) | 120 (± 10) | 45 (± 5) |
| Viscosity at 25°C. (cP) | 85 (± 10) | 115 (± 15) |
| Number-average molecular weight (Mn) | 700 | 2200 |

In what follows, these two commercial products will be called SIL 700 and SIL 2200 for convenience (nomenclature based on their respective molecular weight).

EXAMPLE 1

In this example an anionizable polysiloxane- polyurethane polycondensate was prepared, of theoretical structure:

$$\text{+}(CH_2)_6\text{+}Si(CH_3)_2\text{-}O\text{+}_z Si(CH_3)_2\text{-}(CH_2)_6\text{-}O\text{+}C(=O)\text{-}NH\text{-}R\text{-}NH\text{-}C(=O)\text{+}O\text{-}CH_2\text{-}C(CH_3)(COOH)\text{-}CH_2\text{-}O\text{-}C(=O)\text{-}NH\text{-}R\text{-}NH\text{-}C(=O)\text{+}$$

in which R denotes:

—C₆H₄—CH₂—C₆H₄— and corresponding to the reaction between:

1 mole of SIL 700 (polysiloxane prepolymer)

2 moles of 4,4'-diphenylmethane diisocyanate (called MDI below) and 1 mole of dimethylolpropionic acid (coupling agent, called DMPA below), these values being referred to 1 mole of SIL 700.

50 g of MDI and 50 g of tetrahydrofuran (THF) are introduced, under nitrogen stream, into a cylindrical reactor provided with a central anchor-type stirrer, a thermometer, a condenser, a nitrogen bubbler inlet and supporting a dropping funnel. Dissolving of the mixture takes place with stirring and at ambient temperature.

In parallel, 70 g of SIL 700 have been dissolved in 70 g of THF and the solution thus obtained is poured into the dropping funnel situated above the reactor. This solution of SIL 700 is then introduced, with stirring and nitrogen stream, into the reactor containing the MDI solution, the temperature of the reaction mixture being maintained at 50° C. by external heating. Running-in of the SIL 700 solution takes 1 h 30 min and the temperature of the reaction mixture is maintained at 50° C. throughout the introduction period.

EXAMPLE 3

In this example a cationizable polysiloxane- polyurethane polycondensate was prepared, of theoretical structure:

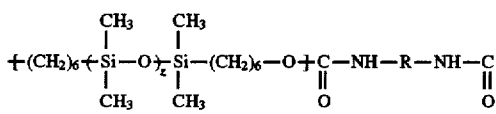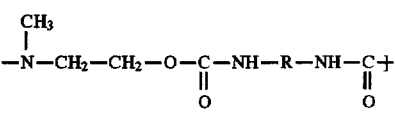

At the end of the running-in, the reaction results in the quantitative formation of a polysiloxane prepolymer with α,ω-diisocyanate ends.

A solution of DMPA obtained by dissolving 13.4 g of DMPA in 400 g of THF is next introduced (pouring time:30 min) into the reactor containing the above prepolymer, this still being done with stirring, bubbling nitrogen and keeping the temperature at 50° C. At the beginning of the pouring, 0.15 g of dibutyltin dilaurate, used as catalyst, is additionally introduced into the reaction mixture. The whole is then allowed to react for 10 h, with stirring and at 50° C. The end of the reaction can be checked by verifying the absence of —N═C═O absorption bands at 2270 cm$^{-1}$ by infrared analysis. If need be, ethanol can then be added to the reaction mixture to terminate the reaction and to consume completely the —N═C═O groups which are still available; in this case it is possible, for example, to add of the order of 10 ml of ethanol and to allow the whole to react again for 4 h at 50° C.

At the end of reaction an organic (THF) solution of the desired polycondensate is obtained, the latter being next recovered and purified by precipitation of said solution into 5 l of an equal-volume (50/50) mixture of petroleum ether and ethyl ether. The recovery yield is 90% by weight after drying. The acid value of the polycondensate obtained is 46 (theoretical: 42). Its number-average molecular weight is 5000.

EXAMPLE 2

The preparation of an anionizable polysiloxane-polyurethane polycondensate with the same theoretical structure as that of Example 1, but this time obtained from the SIL 2200 polysiloxane prepolymer, is undertaken here.

The operating method followed is therefore identical with that of Example 1 but the quantities of reactants introduced this time are the following:

80 g of SIL 2200 dissolved in 80 g of THF
18.2 g of MDI dissolved in 20 g of THF
4.9 g of DMPA dissolved in 200 g of THF
0.1 g of dibutyltin dilaurate so as to conform, here too, to the proportions of 1 mole of SIL 2200:2 moles of MDI:1 mole of DMPA.

In addition, the recovery and the purification of the desired final polycondensate is this time carried out more simply by precipitation of the organic solution containing it into 5 l of deionized water. The recovery yield is then 92% by weight.

The acid value of the polycondensate obtained is 21.7 (theoretical:19.8). Its number-average molecular weight is 6300.

in which R denotes:

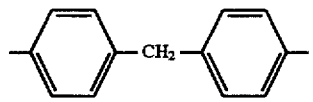

and corresponding to the reaction between:
1 mole of SIL 700
2 moles of MDI
1 mole of N-methyldiethanolamine (coupling agent, called MEA below)
these values being referred to 1 mole of SIL 700.

60 g of MDI and 50 g of THF are introduced, under nitrogen stream, into the same reactor as that of Example 1 and equipped in the same way. Dissolving of the mixture takes place with stirring and at ambient temperature.

In parallel, 70 g of SIL 700 have been dissolved in 70 g of THF and the solution thus obtained is poured into the dropping funnel situated above the reactor. This SIL 700 solution is then introduced, with stirring and under a nitrogen stream, into the reactor containing the MDI solution, the temperature of the reaction mixture being maintained at 50° C. by external heating. Running-in of the SIL 700 solution takes 1 h 30 min and the temperature of the reaction mixture is maintained at 50° C. throughout the introduction period. At the end of the pouring the reaction mixture is diluted with 350 g of THF while the temperature is maintained at 50° C. The reaction has resulted in the quantitative formation of a polysiloxane prepolymer with α,ω-diisocyanate ends.

A solution of MEA, obtained by dissolving 12.5 g of MEA in 70 g of THF is next introduced (pouring time: 30 min) into the reactor containing the above prepolymer, this being done still with stirring, bubbling nitrogen and maintaining the temperature at 50° C. The whole is then allowed to react for 7 h with stirring and at 50° C.

The end of the reaction can be checked by verifying the absence of —N═C═O absorption bands at 2270 cm$^{-1}$ by infrared analysis. If need be, ethanol can then be added to the reaction mixture to terminate the reaction and to consume completely the —N═C═O groups still available; in this case it is possible, for example, to add of the order of 10 ml of ethanol and to leave the whole to react again for 4 h at 50° C.

At the end of reaction an organic (THF) solution of the desired polycondensate is obtained, the latter being next recovered and purified by precipitation of said solution in 5 l of an equal-volume (50/50) mixture of petroleum ether and ethyl ether. The recovery yield is 93% by weight after drying.

The amine value of the polycondensate obtained is 45.7 (theoretical:43). Its number-average molecular weight is 12,600.

EXAMPLE 4

The preparation of a cationizable polysiloxane-polyurethane polycondensate with the same theoretical structure as that of Example 3, but this time obtained from the SIL 2200 polysiloxane prepolymer is undertaken here.

The operating method followed is therefore identical with that of Example 3, but the quantities of reactants introduced this time are the following:

80 g of SIL 2200 dissolved in 80 g of THF
18.2 g of MDI dissolved in 20 g of THF
4.55 g of MEA dissolved in 25 g of THF so as to conform, here too, to the proportions of 1 mole of SIL 2200:2 moles of MDI:1 mole of MEA.

In addition, the recovery and the purification of the desired final polycondensate is this time performed more simply by precipitation of the organic solution containing it into 5 l of deionized water. The recovery yield is then 90% by weight.

The acid value of the polycondensate obtained is 19 (theoretical:20.7). Its number-average molecular weight is 50,100.

EXAMPLE 5

In this example the production of an anionic pseudolatex was undertaken starting with the anionizable polysiloxane-polyurethane polycondensate prepared in Example 1, the said polycondensate being here 50% (according to the acid value) neutralized in situ with sodium hydroxide.

30 g of the polycondensate as obtained directly in Example 1 are dissolved in 170 g of THF (solution containing 15% by weight of polycondensate). The organic solution thus obtained is placed in a reactor and stirred vigorously with a shearing disperser of the Ultra-Turak type. An aqueous phase obtained by mixing 53.8 g of deionized water and 6.16 g of 2 M NaOH (quantity of neutralizing agent needed to neutralize 50% of the —COOH groups carried by the polycondensate) is then introduced dropwise into the reactor containing the stirred organic solution. After complete introduction of the aqueous phase, 140 g of deionized water are next added, still with stirring, so as to dilute the emulsion and to produce complete phase inversion. Stirring is then continued for another 15 min.

The organic solvent is then evaporated selectively from the emulsion by virtue of a rotary evaporator under partial vacuum, care being taken not to exceed a temperature of 50° C., and the aqueous dispersion of polycondensate is finally concentrated to the desired final solids content, which is 25% by weight in this case. A stable pseudolatex of milky appearance is thus obtained.

The mean size of the particles contained in the pseudolatex is 120 nanometers and their size polydispersity is lower than 0.1 (measurements by quasielastic light scattering in a Coulter N4 SD instrument marketed by the Coultronix company).

The pH of the dispersion is 6.6.

When evaporated on a support, this dispersion gives a continuous and uniform film, this being without any addition of plasticizer.

EXAMPLE 6

In this example the production of an anionic pseudolatex was undertaken starting with the anionizable polysiloxane-polyurethane polycondensate prepared in Example 2, the said polycondensate being here 50% (according to the acid value) neutralized in situ with sodium hydroxide.

The operating method is absolutely identical with that shown in Example 5, but the quantities and the nature of the reactants involved this time are the following:

organic solution: 30 g of the polycondensate obtained in Example 2, dissolved in 170 g of THF aqueous phase containing the neutralizing agent: mixture of 27 g of deionized water and 2.7 g of 2 M NaOH quantity of water added for diluting the emulsion:170 g.

An anionic pseudolatex is thus finally obtained, exhibiting the following characteristics:

solids content: 25% by weight
pH: 7.3
mean particle size: 92 nanometers
polydispersity: 0.25

As in Example 5, the pseudolatex obtained gives a continuous and uniform film after evaporation on a support, this being without the presence of plasticizer.

EXAMPLE 7

In this example the production of a cationic pseudolatex was undertaken, starting with the cationizable polysiloxane-polyurethane polycondensate prepared in Example 3, the said polycondensate being in this case 30% (according to the amine value) neutralized in situ with hydrochloric acid.

The operating method is absolutely identical with that shown in Example 5, but the quantities and the nature of the reactants involved this time are the following:

organic solution: 30 g of the polycondensate obtained in Example 3, dissolved in 170 g of THF aqueous phase containing the neutralizing agent: mixture of 27 g of deionized water and 3.4 g of 2 M HCl quantity of water added for diluting the emulsion: 170 g.

A cationic pseudolatex is thus finally obtained, exhibiting the following characteristics:

solids content: 20% by weight
pH: 4.7
mean particle size: 54 nanometers
polydispersity: 0.1

As in Example 5, the pseudolatex obtained gives a continuous and uniform film after evaporation on a support, this being without the presence of plasticizer.

EXAMPLE 8

In this example the production of a cationic pseudolatex was undertaken starting with the cationizable polysiloxane-polyurethane polycondensate prepared in Example 4, the said polycondensate being in this case 70% (according to the amine value) neutralized in situ with hydrochloric acid.

The operating method is absolutely identical with that shown in Example 5, but the quantities and the nature of the reactants involved this time are the following:

organic solution: 30 g of the polycondensate obtained in Example 4, dissolved in 70 g of THF aqueous phase containing the neutralizing agent: mixture of 40 g of deionized water and 3.9 g of 2 M HCl quantity of water added for diluting the emulsion: 60 g.

A cationic pseudolatex is thus finally obtained, exhibiting the following characteristics:

solids content: 20% by weight
pH: 4.28 mean particle size: 75 nanometers
polydispersity: 0.25

As in Example 5, the pseudolatex obtained gives a continuous and uniform film after evaporation on a support, this being without the presence of plasticizer.

EXAMPLE 9

An example of formulation for nail varnish is given here.

| | |
|---|---|
| - pseudolatex of Example 5 | 24.88 g as active |
| - nonionic urethane associative thickener sold under the name of "Seradex 1100" by the Servo company | 0.3 g |
| - pigments | 1 g |
| - water in a quantity sufficient to obtain | 100 g of formulation |

The nail varnish obtained is very resistant to water: the film is intact after 1 hour with stirring in water. The hardness of the film obtained is very satisfactory and the latter adheres properly to the nail keratin without flaking off. It is not tacky and resists scratching. The varnish obtained according to the invention is easily applied on to the nail and additionally exhibits a very good gloss, as well as a satisfactory behaviour.

EXAMPLE 10

This example illustrates a formulation for mascaras.

| | |
|---|---|
| Phase A: | |
| - triethanolamine stearate | 11.8 g |
| - beeswax | 5 g |
| - carnauba wax | 3 g |
| - paraffin wax | 1 g |
| Phase B: | |
| - black iron oxide | 5 g |
| Phase C: | |
| - gum arabic | 2 g |
| - hydroxyethyl cellulose sold under the name of "Cellosize QP" by the Amerchol company | 1.2 g |
| Phase D: | |
| - pseudolatex of Example 6 | 5 g active substance |
| - a quanitity sufficient of preserving agent | |
| - water in a quantity sufficient to obtain | 100 g of formulation |

This mascara is obtained by heating the ingredients of Phase A to 85° C., to which Phase B is added, and mixing is carried out with the aid of a turbine. The water of preparation is then heated to boiling, the preserving agents are added and then, at 85° C., the ingredients of Phase C are added.

The aqueous phase obtained (85° C.) is then added to Phase A (85° C.) with stirring with the aid of a turbine (emulsifying) and then the pseudolatex of Phase D is finally added at 30° C., and the mixture is stirred with a blade.

EXAMPLE 11

This example illustrates another composition for mascaras. This mascara is prepared according to the same operating method as that given in Example 10, but with the following constituents:

| | |
|---|---|
| Phase A | |
| - glycerol stearate | 3 g |
| - mixture of esters of lauric acid and of sorbitol and of lauric acid and of sorbitol oxyethylenated with 20 moles of ethylene oxide, sold under the name of "Tween 20" by ICI | 3.7 g |
| - monoesters of stearic acid and of sorbitan, sold under the name of "Span 60" by ICI | 5.6 g |
| - beeswax | 6 g |
| - carnauba wax | 1.8 g |
| - paraffin wax | 7.8 g |
| Phase B: | |
| - black iron oxide | 4.5 g |
| Phase C: | |
| - hydroxyethyl cellulose sold under the name of "Cellosize QP" by the Amerchol company | 1.5 g |
| Phase D: | |
| - pseudolatex of Example 7 | 2 g |
| - quantity sufficient of preserving agents | |
| - water in a quantity sufficient to obtain | 100 g of formulation |

EXAMPLE 12

Four examples of hair-care formulations are given here.

Styling lotion:

| | |
|---|---|
| - pseudolatex of Example 5 | 5 g of active substance |
| - a quantity sufficient of perfumes, dyes, preserving agents | |
| - deionized water in a quantity ufficient to obtain | 100 g of lotion |

This composition, applied to hair after a shampoo, imparts a good form-retention to the hairstyle and a very good sheen to the hair.

Styling lotion:

| | |
|---|---|
| - pseudolatex of Example 6 | 4 g of active substance |
| - a quantity sufficient of perfumes, dyes, preserving agents | |
| - deionized water in a quantity sufficient to obtain | 100 g of lotion |

This composition, applied to hair after a shampoo, imparts good form-retention to the hairstyle and a very good sheen to the hair.

Setting spray:

A setting spray is prepared in a pump bottle by packaging the following composition in an appropriate container:

| | |
|---|---|
| - pseudolatex of Example 7 | 3 g of active substance |
| - a quantity sufficient of perfumes, dyes, preserving agents | |
| - deionized water in a quantity sufficient to obtain | 100 g of spray |

The container, once filled, is then fitted with a spraying pump. This composition imparts good behaviour to the hairstyle and a very good sheen to the hair.

Setting spray:

A setting spray is prepared by mixing:

| | |
|---|---|
| - pseudolatex of Example 8 | 3 g of active substance |
| - a quantity sufficient of perfumes, dyes, preserving agents | |
| - deionized water in a quantity sufficient to obtain | 100 g of lotion | the lotion obtained being then packaged in a sprayer which can be recharged with compressed air. This composition imparts good behaviour to the hairstyle and a very good sheen to the hair.

What is claimed is:

1. A cosmetic composition comprising a cosmetically acceptable carrier and at least one pseudolatex based on a multiblock polycondensate which comprises, as a first component, a polysiloxane block corresponding to the following formula (I):

$$+\!\!+\!\!-X^1-P-X^1\!\!+\!\!\underset{\underset{O}{\|}}{C}-NH-R-NH-\underset{\underset{O}{\|}}{C}+ \quad (I)$$

in which:

P is a polysiloxane block corresponding to the following formula (I'):

$$-Y\!\!+\!\!\underset{\underset{R^1}{|}}{\overset{R^1}{|}}{Si}-O\!\!+_{\!z}\!\!\underset{\underset{R^1}{|}}{\overset{R^1}{|}}{Si}-Y- \quad (I')$$

wherein:

the radicals $R^1$, which may be identical or different, are monovalent radicals selected from the group consisting of phenyl, naphthyl, benzyl, phenylethyl, tolyl, and xylyl radicals, or are nonaromatic $C_1$-$C_{20}$ hydrocarbon radicals;

Y denotes a divalent hydrocarbon radical, or z is an integer such that the mean molecular weight of the polysiloxane block ranges from 300 to 10,000.

$X^1$, each of which can be identical or different, denotes —O— or —NH—, and

R is

[cyclohexylene structure],

[methylcyclohexylene structure],

[naphthylene structure],

[bis-phenyl-$(CH_2)_b$- structure], or

—$(CH_2)_c$— in which b is an integer from 0 to 3 and c is an integer from 1 to 20;

and, as a second component, a block of polyurethane, polyurea, or a combination thereof, said second component further comprising anionic or cationic groups and corresponding to the formula (II):

$$+\!\!+\!\!-X^2-B-X^2-\underset{\underset{O}{\|}}{C}-NH-R-NH-\underset{\underset{O}{\|}}{C}+_{\!x}\!\!+ \quad (II)$$

wherein:

$X^2$, each of which can be identical or different, denotes —O— or —NH—,

R is as defined above for formula (I), x is an integer from 1 to 10, and

B is a a divalent hydrocarbon radical which carries a group containing at least one carboxylic functional group, at least one sulphonic functional group, or a combination of at least one carboxylic functional group and at least one sulphonic functional group, said at least one carboxylic functional group, said at least one sulphonic functional group, or said combination having been neutralized with an inorganic or organic base, to provide a negative ionic charge or a divalent hydrocarbon radical which carries at least one tertiary amine group, said at least one tertiary amine group having been neutralized with an inorganic or organic acid or quaternized with an alkyl halide, to provide a positive ionic charge.

2. The composition according to claim 1, wherein the number-average molecular weight of said multiblock polycondensate ranges from 2000 to 500,000.

3. The composition according to claim 2, wherein said number-average molecular weight ranges from 3000 to 250,000.

4. The composition according to claim 1, wherein the number ratio of the blocks of polyurethane, polyurea, or a combination thereof to the blocks of polysiloxane in the multiblock polycondensate ranges from 1:1 to 10:1.

5. The composition according to claim 4, wherein said number ratio ranges from 1:1 to 3:1.

6. The composition according to claim 1, wherein the degree of neutralization or of quaternization ranges from 10 to 100%.

7. The composition according to claim 6, wherein said degree ranges from 20 to 100%.

8. The composition according to claim 1, wherein the degree of neutralization ranges from 10 to 100%.

9. The composition according to claim 8, wherein said degree ranges from 20 to 100%.

10. The composition according to claim 1, wherein said divalent radical Y an alkylene radical of formula —$(CH_2)_a$—, in which a denotes an integer which may range from 1 to 10.

11. The composition according to claim 1, wherein the radicals $R^1$ independently are $C_1$-$C_{20}$ alkyl radicals, cyclohexyl radicals, phenyl radicals, or naphthyl radicals.

12. The composition according to claim 11, wherein the radicals $R^1$ are methyl, ethyl, propyl, isopropyl, butyl, pentyl, hexyl, octyl, decyl, dodecyl, octadecyl, cyclohexyl, phenyl, naphthyl, benzyl, phenylethyl, tolyl, or xylyl radicals.

13. The composition according to claim 1, wherein the polysiloxane block P corresponds to the following formula (I''):

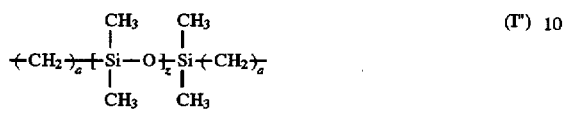

in which a denotes an integer from 1 to 10 and z is an integer such that the mean molecular weight of the polysiloxane block ranges from 300 to 10,000.

14. The composition according to claim 1, wherein x is from 1 to 3.

15. The composition according to claim 1, wherein the radical B corresponds to the formula (III):

in which $R^2$ denotes a $C_1$–$C_3$ linear or branched alkyl radical, Z is a carboxylic acid anion (—COO$^-$), a salt thereof, a sulphonic acid anion (—SO$_3$), or a salt thereof and p and q, which may be identical or different, denote integers from 1 to 5.

16. The composition according to claim 1, wherein the radical B corresponds to the formula (III'):

in which Z is a carboxylic acid (—COO$^-$) anion, a sulphonic acid (—SO$_3^-$) anion, or a salt thereof.

17. The composition according to claim 1, wherein the radical B, in neutralized or quaternized form, corresponds to the following formula (IV'):

in which $R^3$ denotes a $C_1$–$C_4$ linear or branched alkyl radical, r and s are identical or different integers which may be from 1 to 10, and $R^4$ denotes hydrogen, a $C_1$–$C_{10}$ linear or branched alkyl radical, a phenyl radical, or a naphthyl radical.

18. The composition according to claim 1, wherein c is from 2 to 12.

19. The composition according to claim 1, wherein said radical R is a hexamethylene, 4,4'-biphenylenemethane, 2,4-tolylene, 2,6-tolylene, 1,5-naphthylene, p-phenylene or 4,4-methylenebiscyclohexyl radical or the divalent radical derived from isophorone.

20. The composition according to claim 1, wherein said multiblock polycondensate has been obtained by a process comprising the steps of:

(a) reacting, in a first stage, (i) a polysiloxane polymer which is α,ω-dihydroxypolysiloxane or α,ω-diaminopolysiloxane or α,ω-aminohydroxy- or hydroxyaminopolysiloxane with (ii) a diisocyanate, said diisocyanate being present in stoichiometric quantity or in stoichiometric excess, whereby a polysiloxane is obtained containing an isocyanate functional group at each of its chain ends;

(b) then, in a second stage, coupling the chains of the polysiloxane obtained previously in step (a) by reaction with a at least one coupling agent, wherein said coupling agent is a diol, a diamine, or an alcoholamine, said coupling agent carrying cationizable or anionizable groups; and, (c) finally, in a third stage, partially or completely ionizing the cationizable or anionizable groups of the polycondensate obtained at the end of the second stage (b) to obtain said anionic or cationic groups.

21. The composition according to claim 20, wherein the degree of ionization ranges from 10 to 100%.

22. The composition according to claim 21, wherein the degree of ionization ranges from 20 to 100%.

23. The composition according to claim 20, wherein the starting polysiloxane polymer corresponds to the formula:

$$X^3\text{—P—}X^3$$

in which P corresponds to the following formula (T):

in which the radicals $R^1$, which may be identical or different, are monovalent phenyl or naphthyl radicals or nonaromatic $C_1$–$C_{20}$ hydrocarbon radicals, Y denotes a divalent hydrocarbon radical and z is an integer such that the mean molecular weight of the polysiloxane block ranges from 300 to 10,000, and $X^3$, each of which can be identical or different, denotes —OH or —NH$_2$.

24. The composition according to claim 20, wherein the diisocyanate corresponds to the formula:

$$O\!=\!C\!=\!N\text{—R—}N\!=\!C\!=\!O$$

in which R is

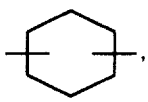

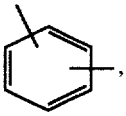

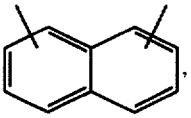

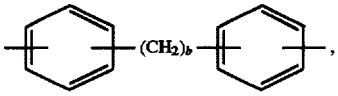

-continued

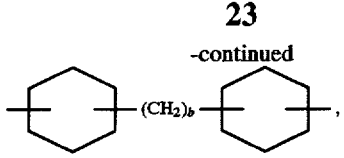

or

wherein b is an integer from 0 to 3 and c is an integer from 1 to 20.

25. The composition according to claim 20, wherein the coupling agent corresponds to the formula:

$$X^4—B—X^4$$

in which B is a divalent radical carrying a positive or negative ionic charge and $X^4$ denotes —OH or —$NH_2$.

26. The composition according to claim 1, wherein the mean size of the particles contained in said pseudolatex ranges from 5 to 400 nanometers.

27. The composition according to claim 26, wherein the mean size of said particles contained in said pseudolatex ranges from 10 to 250 nanometers.

28. The composition according to claim 1, wherein the size polydispersity of the particles contained in said pseudolatex, measured by quasielastic light scattering, is lower than 0.5.

29. The composition according to claim 28, wherein the size polydispersity of the particles contained in said pseudolatex, measured by quasielastic light scattering, is lower than 0.3.

30. The composition according to claim 1, wherein said cosmetic composition is a hair-care composition.

31. The composition according to claim 1, wherein said cosmetic composition is a make-up composition.

32. The composition according to claim 1, wherein said cosmetic composition is a nail varnish.

33. The composition according to claim 1, wherein said cosmetic composition is a mascara.

34. The composition according to claim 1, wherein said cosmetic composition is a composition for skin care.

35. The composition according to claim 1, wherein said cosmetic composition is an antisun composition.

36. A process for the treatment of keratinous matter, comprising applying to said keratinous matter a cosmetic composition comprising a cosmetically acceptable carrier and at least one pseudolatex based on a multiblock polycondensate which comprises, as a first component, a polysiloxane block corresponding to the following formula (I):

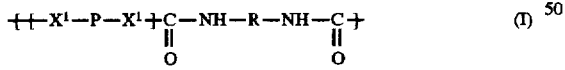 (I)

in which:

P is a polysiloxane block corresponding to the following formula (I'):

 (I')

wherein:

the radicals $R^1$, which may be identical or different, are monovalent radicals selected from the group consisting of phenyl, naphthyl, benzyl, phenylethyl, tolyl, and xylyl radicals, or are nonaromatic $C_1$–$C_{20}$ hydrocarbon radicals;

Y denotes a divalent hydrocarbon radical, or z is an integer such that the mean molecular weight of the polysiloxane block ranges from 300 to 10,000, $X^1$, each of which can be identical or different, denotes —O— or —NH—, and R is

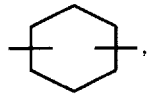

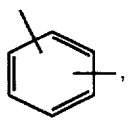

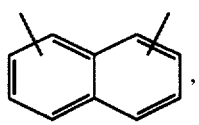

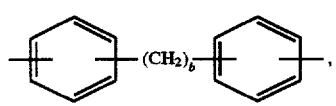

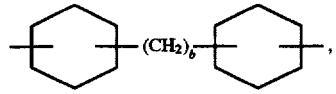

or

in which b is an integer from 0 to 3 and c is an integer from 1 to 20;

and, as a second component, a block of polyurethane, polyurea, or a combination thereof, said second component further comprising anionic or cationic groups and corresponding to the formula (II):

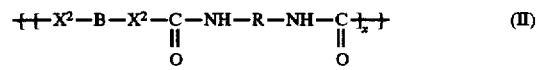 (II)

wherein:

$X^2$, each of which can be identical or different, denotes —O— or —NH—,

R is as defined above for formula (I), x is an integer from 1 to 10, and

B is a divalent hydrocarbon radical which carries a group containing at least one carboxylic functional group, at least one sulphonic functional group, or a combination of at least one carboxylic functional group and at least one sulphonic functional group, said at least one carboxylic functional group, said at least one sulphonic functional group, or said combination having been neutralized with an inorganic or organic base, to provide a negative ionic charge or a divalent hydrocarbon radical which carries at least one tertiary amine group, said at least one tertiary amine group having been neutralized with an inorganic or organic acid or quaternized with an alkyl halide, to provide a positive ionic charge.

37. A process as claimed in claim 36, wherein said cosmetic composition is a hair care composition.

38. A process as claimed in claim 36, wherein said cosmetic composition is a make-up composition.

39. A process as claimed in claim 36, wherein said cosmetic composition is a nail varnish.

40. A process as claimed in claim 36, wherein said cosmetic composition is a mascara.

41. A process as claimed in claim 36, wherein said cosmetic composition is a composition for skin care.

42. A process as claimed in claim 36, wherein said cosmetic composition is an anti-sun composition.

43. A cosmetic composition according to claim 1, wherein said composition further comprises at least one cosmetic additive selected from fatty substances, organic solvents, silicons, thickening agents, softeners, antifoaming agents, hydrating agents, moisturizers, treating agents, anionic, nonionic and amphoteric polymers, antiperspirants, alkalifying agents, dyes, pigments, perfumes, preserving agents and propellent agents.

44. A method of forming a film in a cosmetic composition comprising the step of using in a cosmetic composition a film-forming agent comprising at least one pseudolatex based on a multiblock polycondensate which comprises, as a first component, a polysiloxane block corresponding to the following formula (I):

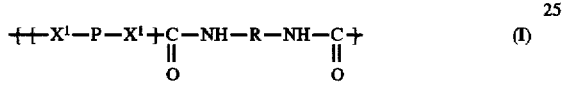  (I)

in which:

P is a polysiloxane block corresponding to the following formula (T):

  (T)

wherein:

the radicals $R^1$, which may be identical or different, are monovalent radicals selected from the group consisting of phenyl, naphthyl, benzyl, phenylethyl, tolyl, and xylyl radicals, or are nonaromatic $C_1$–$C_{20}$ hydrocarbon radicals;

Y denotes a divalent hydrocarbon radical, or z is an integer such that the mean molecular weight of the polysiloxane block ranges from 300 to 10,000, $X^1$, each of which can be identical or different, denotes —O— or —NH—, and R is

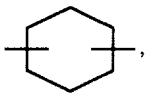

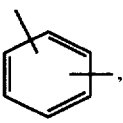

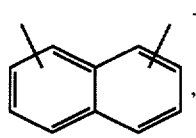

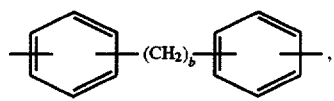

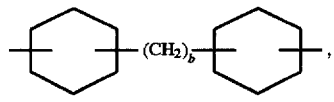

or

—(CH₂)_c— in which b is an integer from 0 to 3 and c is an integer from 1 to 20;

and, as a second component, a block of polyurethane, polyurea, or a combination thereof, said second component further comprising anionic or cationic groups and corresponding to the formula (II):

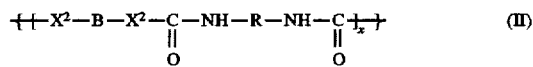  (II)

wherein:

$X^2$, each of which can be identical or different, denotes —O— or —NH—,

R is as defined above for formula (I), x is an integer from 1 to 10, and

B is a divalent hydrocarbon radical which carries a group containing at least one carboxylic functional group, at least one sulphonic functional group, or a combination of at least one carboxylic functional group and at least one sulphonic functional group, said at least one carboxylic functional group, said at least one sulphonic functional group, or said combination having been neutralized with an inorganic or organic base, to provide a negative ionic charge or a divalent hydrocarbon radical which carries at least one tertiary amine group, said at least one tertiary amine group having been neutralized with an inorganic or organic acid or quaternized with an alkyl halide, to provide a positive ionic charge.

* * * * *

UNITED STATES PATENT AND TRADEMARK OFFICE
CERTIFICATE OF CORRECTION

PATENT NO. : 5,643,581
DATED : July 1, 1997
INVENTOR(S) : Nathalie MOUGIN and Jean MONDET It is certified that error appears in the above-indentified patent and that said Letters Patent is hereby corrected as shown below:

<u>In the Claims</u>, claim 1, column 20, line 27, delete "a" (second occurrence).

claim 10, column 20, line 62, after "Y" insert --is--.

claim 15, column 21, line 29, change "(—$SO_3$)" to --(—$SO_3^-$)--.

Signed and Sealed this

Ninth Day of September, 1997

BRUCE LEHMAN

*Attest:*

*Attesting Officer*       *Commissioner of Patents and Trademarks*